US006998479B1

(12) United States Patent
Khomutov et al.

(10) Patent No.: US 6,998,479 B1
(45) Date of Patent: Feb. 14, 2006

(54) DERIVATIVES OF CYCLODEXTRINS (76) Inventors: Alexei Khomutov, Apartment 447, Lyusinovskaya Street 68, Moscow, 113162 (RU); Dmitry Yakovlev, Apartment 46 Profsoyusnaya Street 114-6, Moscow 117437 (RU); Radii Khomutov, Apartment 46, Profsoyusnaya Street 43-1, Moscow, 117420 (RU); Timo Korpela, Kasarminkatu 5 as 8, FIN-20500 Turku (FI)

( * ) Notice: Subject to any disclaimer, the term of this patent is extended or adjusted under 35 U.S.C. 154(b) by 0 days.

(21) Appl. No.: 09/623,364

(22) PCT Filed: Mar. 4, 1999

(86) PCT No.: PCT/FI99/00167

§ 371 (c)(1),
(2), (4) Date: Oct. 23, 2000

(87) PCT Pub. No.: WO99/45032

PCT Pub. Date: Sep. 10, 1999

(30) Foreign Application Priority Data

Mar. 4, 1998 (FI) .................... 980489

(51) Int. Cl.
*C08B 37/16* (2006.01)
*C08B 37/00* (2006.01)

(52) U.S. Cl. ................ 536/46; 536/18.7
(58) Field of Classification Search ........ 536/46, 536/18.7

See application file for complete search history.

(56) References Cited

FOREIGN PATENT DOCUMENTS

WO    A2-9641813    12/1996

OTHER PUBLICATIONS

Nedospasov et al., STN International, No. 5, pp. 1136-1141 (1976), Izv. Akad Nauk SSSR, Ser. Khim (1976), (5) 1136-41.
Varaprasad et al., Bioorganic Chemistry, vol. 14, pp. 8-16 (1986).
Nedospasov et al, STN Internatinal, No. 4, pp. 962-964 (1978), Izv. Akad. Nauk SSSR, Ser. Khim. (1978), (4) 962-4.
AS USSR Molecular et al., WPI/Derwent, No. 88-153418 (1987).
Mortellaro et al., Bioorganic and Medical Chemsitry Letters, vol. 4, No. 16, pp. 2041-2044 (1994).
Hori et al., STN International, pp. 602-608 (1998), Nippo Kagaku Kaishi (1998), (9), 602-608.

*Primary Examiner*—James O. Wilson
*Assistant Examiner*—Everett White
(74) *Attorney, Agent, or Firm*—Birch, Stewart, Kolasch & Birch, LLP (57) ABSTRACT

The present invention is directed to novel aminooxy-cyclodextrin derivatives of the formula (1): CD—(X—Y—ONH$_2$)$_n$, wherein CD is mono- or polydeoxy α-, β-, or γ-cyclodextrin, carrying in its 6-, 3- and/or 2-position a group containing the aminooxy group, and optionally carrying substituents different from (X—Y—ONH$_2$). Y is a linker group between the aminooxy group and the mono- or polydeoxy-CD group, X is a functional group or an atom necessary to connect the linker Y and the deoxy CD group, or Y is a direct bond when X is a direct bond, and n is $\geq 1$, but $\leq 24$, 21 and 18 for α-, β- or γ-cyclodextrin, respectively, the protected aminooxy derivatives thereof, as well the methods for their preparation and use.

9 Claims, 4 Drawing Sheets

DERIVATIVES OF CYCLODEXTRINS

This application is the national phase under 35 U.S.C. § 371 of PCT International Application No. PCT/FI99/00167 which has an International filing date of Mar. 4, 1999, which designated the United States of America.

FIELD OF THE INVENTION

This invention relates to the design and synthesis of earlier unknown chemical derivatives of cyclodextrins. The novel compounds exert a number of useful properties which make them applicable as complexants, solubilizers, carbonyl reagents, catalysts, or starting materials for the synthesis of products to be employed in pharmaceuticals, cosmetics, agriculture or in scientific laboratories.

BACKGROUND OF THE INVENTION

α-, β- and γ-Cyclodextrins (α-CD, β-CD and γ-CD) are cyclic oligosacharides consisting of 6, 7 or 8 glucopyranose units, respectively, which are joined together by α(1–4) linkages:

m = 6  α - CD
m = 7  β - CD
m = 8  γ - CD

Cyclodextrins (termed hosts) can imbibe certain molecules or parts thereof (termed guests) into their center cavities. The noncovalent reversible adducts or inclusion complexes formed between the host and the quest can drastically change the properties of the parent guest molecules in diverse ways, such as to increase solubility, decrease volatility, protect from chemical or light-catalyzed reactions, change the location of absorption of complexed drugs in the intestine, etc.

Parent CDs can be covalently modified with a number of reagents to form chemical derivatives. The derivatives can normally bind similar guest compounds as do the parent CDs, but the properties of the complexes can be changed, A description on the syntheses of CD derivatives and the properties of inclusion complexes of both parent and modified cyclodextrins can be found for instance in Croft, A. P. & Bartsch, R. A. "Synthesis of Chemically Modified Cyclodextrins", *Tetrahedron*, 1983, V. 39, No 9, P. 1417–1471 Szejtli, J. "Cyclodextrin Technology", Kluwer Academic Publishers, Dordrecht, 1988, pp. 1–450.

Some derivatives of β-CD have a higher solubility than do the parent compound and hence they are often preferable complexants and solubilizers. The potential of the chemical derivatives of β-CD is amplified by its low price as a starting material in comparison to α- and γ-CDs. In contrast to β-CD, the more expensive α- and γ-CDs are readily water soluble and can be used without chemical derivatization for certain purposes. This is illustrated by a number of reports on their complexes with various guest compounds such as steroid hormones, cholesterol or its derivatives and with some drugs. Appropriately alkylated or hydroxyalkylated γ-CDs are also good complexants since their inclusion complexes do not precipitate even at high concentration, as stated in EP 06792.

A large number of papers deals with the syntheses of CD chemical derivatives and their application for divergent purposes (see e.g. Szejtli, J "Cyclodextrin Technology" 1988) clearly showing the importance of the CD derivatives.

SUMMARY OF THE INVENTION

The present invention describes novel CD derivatives carrying specific functions containing an aminooxy ($H_2NO$—) group covalently connected to a glucopyranose unit of CD. These derivatives have significantly different properties from the CD derivatives known in the prior art and thus they enlarge the area of application of CDs. The present invention also describes the preparation and use of the said novel CD derivatives as such or complexed with guest molecules or further chemically modified.

DETAILED DESCRIPTION OF THE INVENTION

The present invention is related to an earlier unknown type of α-, β- or γ-CD chemical derivatives containing the aminooxy ($R_2NO$—) functional group attached to the CD core and having the general formula 1:

formula 1 wherein CD is mono- or polydeoxy α-, γ- or γ-CD, carrying in its 6-, 3- and/or 2-position the aminooxy function containing group, and wherein Y is a linker arm connected to deoxy-CD by means of X, which is a direct bond, or a functional group or an atom necessary to connect the linker Y and the deoxy-CD, whereby Y is a direct bond when X is a direct bond. The integer n is equal to or larger than one and cannot be more then 18, 21 and 24 for α-, β and γ-CD, respectively.

The invention also relates to the compounds of the formula 1, wherein the aminooxy group is in protected form, especially in the form of the 1-ethoxy-ethylideneaminooxy group, —O—N=$C(CH_3)OC_2H_5$, or as the acetone oxime group, —O—N=$C(CH_3)_2$.

The aminooxy-CDs of formula 1 preferably carry one or several $H_2NO$-groups attached to 6-hydroxy groups (see examples I–IV). By utilizing the different reactivities of primary and secondary hydroxyl groups (primary hydroxyls more reactive than secondary), and if necessary, suitably protected hydroxyl groups, one can discriminate between the reaction at the "top", (primary) hydroxyls and at the "bottom" (secondary) hydroxyls of the CD molecule (see Croft et. al. supra). These latter types may be important for synthetizing artificial receptors, carriers and catalysts based on the CD-core.

In the compound of the formula 1, CD is a mono- or polyde-oxy α-, β- or γ-cyclodextrin. In these compounds, one or more hydroxy groups in the positions 6, 3 and/or 2 of CD are replaced with a (X—Y—$ONH_2$) fragment, and specifically, together with primary hydroxy groups, one or more secondary hydroxy group can also be substituted with a (X—Y—ONH$_2$) fragment. The compound according to the invention carrying aminooxy groups can optionally carry further substituents. In the aminooxy-CD, one or more hydroxy groups in the 6-, 3- and/or 2-position may be also substituted e.g. into H$_2$N—, HS—, —COOH, alkoxy, such as C$_1$–C$_6$-alkoxy, aryloxy, aryl being preferably phenyl, benzyl or tolyl, or acyloxy groups, acyl being preferably derived from C$_1$ –C$_6$-carboxylic or benzoic acid. Alkyl-, aryl- and acyloxy may carry additional functional groups in a side chain or aromatic ring.

Y is a "linker arm, or linking group" and serves as, a bridge between the aminooxy (H$_2$NO—) group and the deoxy-CD moiety. Usually Y is alkylene, alkenylene with one or more double bounds which may be either isolated or conjugated, alkynylene with one or more triple bonds which may be either isolated or conjugated, or arylene or arylalkylene fragments where aryl may be substituted or not substituted, such as phenylene. The alkylene, alkenylene and alkynylene fragments may be linear or branched and preferably contain 2–12 C-atoms in the chain. One or more of the chain members (methylene groups) may be replaced by —NH—, —O—, —S—, —S—S—, —C(O)NH, —C(O)O—, —OP(O)(OH)O—, —S(O)—, SO$_2$—, —CHR—, where R is preferably alkyl, aryl, —OR', —NH$_2$, —NHR', —NR'$_2$, —OH, —COOH, or —ONH$_2$, groups and where R' is alkyl, aryl, or acyl. As R and R', aryl is preferably phenyl, aryl lower alkyl, such as benzyl or tolyl.

X is preferably —O—, —S—, —NH—, —NR"—, —OCO—, —NH—O—, =NO—, —NHC(O)—, —OP(O)(OH), —R"C=NO—, where R" is alkyl.

R, R' and R" when having the meaning of alkyl, are preferably linear or branched C$_1$–C$_6$-alkyl, in the meaning of acyl they are preferably derived from linear or branched C$_1$–C$_6$-carboxylic acids or benzoic acid.

In the preferred compounds of formula 1, Y is alkylene or alkenylene of 2–12, preferably 2–6 C-atoms, wherein one or more of the chain members may be replaced by —NH—, =N—O—, —O—, —S—, —C(O)NH—, —C(O)O—, or —CHR$_1$— wherein R$_1$ is methyl, ethyl or propyl and X is —O—, —S—, —NH—, —OC(O)— or —NH—O—.

The compounds of the formula 1 are week bases (usually the pK of the H$_2$NO-group is between 4.0–6.0) and their solubility is different from the parent CD molecules. As indicated by the pK values, a unique possibility exists to regulate the ionic form of the compounds of formula 1 by solvent acidity near the physiological pH-region. That means that a low pH favors complexation of ionic guest molecules, while high pH-values favor the contribution of non-ionic interactions between host and guest. With related compounds containing alkylamino functions, protonation-deprotonation takes place only at around pH 10 (Boger, J. et al *Helv. Chim. Acta,* 1978, V. 61, P. 2190–2218).

The compounds of formula 1 are carbonyl reagents like other O-substituted hydroxylamines. They react rapidly and quantitatively with various aldehydes and ketones forming oximes which have high stability in water solution at a broad range of pHs. These properties of aminooxy-CDs enable the synthesis of a multitude of CD derivatives in addition to those of the formula 1; for example, immobilization of CDs on solid supports and subsequent use in the chromatography of various important compounds such as stereoisomers of pharmaceuticals. In addition, oligo- and polymeric materials are readily obtained in a single-step by allowing dialdehydes or diketones to react with di- or polysubstituted aminooxy-CDs in aqueous solution. Such oligo- or polymeric materials are advantageously used as semipermeable or stereoselective membranes, as prolonged-release supports for drugs, sanitary, cosmetics or agricultural materials. Further, the chemical reactivity properties of the aminooxy functions enable one to stabilize CD-complexes of certain physiologically active, highly reactive, aldehydes and ketones—for instance, steroids, prostaglandins and vitamins—by anchoring these into CDs via the oxime bond in addition to the stabilization involved in the host-guest interaction. Since the stabilization effect is cumulative (not additive), the protection conferred by molecular complexation can be drastically increased.

Inclusion complexes in general may be additionally stabilized by means of oxime formation with a suitable aldehyde or ketone. In this case the inclusion complex is first formed which is then reacted with the aldehyde or ketone to form the inclusion complex oxime. Thus the existence of steric hindrance at the cavity entrance way prevent complex from dissociation.

While the oxime bond is stable in water solutions, especially at extreme pH values, it may slowly decompose. This property can be utilized for the slow release of aminooxy-CD bound drugs in the stomach and intestine.

Since aminooxy-CDs are carbonyl reagents, they may inhibit certain crucial enzymes in the metabolism of cells, such as PLP-, pyruvate-, or ketobutyrate-dependent enzymes. The inhibitory potency will depend on the affinity of the coenzyme to protein.

The existence of aminooxy group(s) bound to a CD molecule means that such compounds, like other O-substituted hydroxylamines, are capable of reacting directly with cytidine and adenosine. This was confirmed by the reaction of aminooxy-CDs of formula 1 with 4-thiouracil, 6-mercaptopurine riboside or their derivatives and even cytidines themself (see examples XIII and XIV). Hence, the compounds of formula 1 can be useful for the modification of nucleotides, nucleosides, bases, nucleoside coenzymes and nucleic acids, such as for the formation of nucleotide and nucleoside pyrimidine and purine derivatives of aminooxy CD, wherein the pyrimidine and purine preferably are cytosine or adenine as such, or in the form of their corresponding derivatives.

At neutral and slightly acidic pH, the aminooxy groups of compound of formula 1 are not protonated. The nonprotonated aminooxy groups are strong nucleophiles capable of reacting with an activated carboxyl group (esters, activated esters, mixed anhydrides, anhydrides, etc.) even in water solutions forming stable hydroxamic acids. These can have new useful properties such as the ability to complex certain metal ions. Combined metal ion and CD complexation functions of the aminooxy-CD derivatives may be used for recovering of metal ions from solutions.

A comparison of the compounds of the present invention with amino group containing CDs (Boger, J. et al. *Helv. Chim. Acta,* 1978, V. 61, P. 2190–2218) demonstrates various advantages for the aminooxy-CDs. The basic disadvantages of the alkylamino-CDs are the high pKs necessitating alkaline reaction conditions during the derivatization reactions and the low stability of the Schiff-base bond between the amino and aldehyde or keto groups in aqueous solutions.

The high nucleophilicity of the aminooxy (H$_2$NO—) group, Suitable compounds (3') are e.g. 4-(ethoxyethylideneamino-oxy) bromobutene-2, ethyl N-(ω-iodoalkyloxy) acetimidate, the sodium salt of 3-(ethoxyethylideneaminooxy)-2-bromo-bromopropionic acids etc. The compounds (3') are used in alkaline water solutions, using e.g. alkali or alkaline-earth metals, or hydrides, hydroxides, oxides, carbonates, hydrocarbonates thereof; or quaternary ammonium salts, mono-, di- and trialkylamines carrying lower ($C_1$–$C_4$) linear or branched alkyl groups being the same or different in alkaline water-organic mixtures (the organic solvent being e.g. a lower (1–4C) alcohol, dioxane, tetrahydrofuran, glyme, cellosolve, dimethylsulfoxide, dimethylformamide) or in liquid ammonia at temperatures from elevated (about 100° C. or higher) to ambient temperature. The substitution degree depends on the reaction conditions and the products can have either only few primary hydroxyls being substituted or also secondary hydroxy groups may be involved in the reaction.

b) Alkylating an activated CD-derivative, such as a tosylate, mesylate, halogen derivative, epoxide, activated ester, with an aminooxy-protected, functionally substituted hydroxylamine (4')

wherein $R'_2$, $R'_3$ and $R'_4$ are hydroxy, or an activated group such as tosyl, mesyl, halogen, ester, epoxide, and X, Y and w are as defined above, and thereafter optionally removing the protecting group. In this reaction, aminooxy CD derivatives are obtained, wherein X is not only O, but also e.g. sulfur or an imino group.

Suitable compounds of the formula (4) are e.g. ethyl N-(ω-mercaptoalkyloxy)-acetimidate, ethyl N-(ω-aminoalkylky-loxy) acetimidate or ethyl N-hydroxyacetimidate itself.

The activated CD-derivative can also be e.g. a mono- or poly-N-hydroxysuccinimide activated CD-derivative having a —COOH group, which is reacted with the compound of formula 4, where X is a HN-group.

According to an embodiment, one or more of the secondary hydroxy groups in the CD derivative may be unsubstituted or substituted with groups other than activating tosyl, mesyl or halogen, such as with those described above.

c) Modifying a functionally-substituted CD derivative having of the formula (5)

(5)

wherein at least one of the groups $R''_2$, $R''_3$, and $R''_4$ mean thiol-, amino- carboxy- etc. group possibly linked directly to deoxy-CD-ring, or mean alkylenoxy- or acyloxy groups, which contain at least one thiol-, amino-, carboxy-, etc. group, or their derivative, and the remaining functional groups are hydroxyl groups or hydroxyl groups at 6-, 3-, and/or 2-position(s) which are substituted with a group, for example, $H_2N$—, HS—, —COOH, alkoxy-, such as $C_1$-$C_6$— alkoxy-, aryloxy-, wherein aryl is preferably phenyl, benzyl, or tolyl, or with acyloxy group, wherein acyl preferably originates from $C_1$-$C_6$— carboxyl, or benzoic acids, and wherein alkyl-, aryl-, and acyloxy- can additionally contain functional groups like $H_2N$—, HS—, —COOH in their structure, in side chain or in aromatic ring, and exist, if necessary, in a protected form, a typical example being unsubstituted alkoxy, aryloxy, or acyloxy, modified with an appropriate aminooxy protected substituted hydroxylamine according to formula (3'), after which the protecting group(s) are removed, or d) with modifying such CD-derivative, having one or more keto or aldehyde function at 2-, 3-, and/or 6-position, optionally joined with the above-described linkers, according to bis-aminooxyalkanes of formula (5')

$$H_2NO(CH_2)_tONH_2 \qquad (5')$$

wherein t=2–12 and wherein one of the methylene groups can be replaced with O or S atoms or —NH— or —S—S— functions.

The cyclodextrin starting materials of the described reactions are well-known from literature.

Selection of a proper protecting group for aminooxy function is crucial, to be succesful in preparing the compounds of formula 1. In the present invention ethyl-N-hydroxyacetimidate fragment or alternatively acetonoxime were employed. Derivatives protected in such a way are stable in a large area of different reaction conditions and the derivatives can be readily converted to corresponding O-substituted hydroxylamines by acid treatment. In the case of ethoxylidene protection the masking group can be removed within 10–60 min at the room temperature with a diluted strong acid, exemplified by hydrohalides, sulfuric phosphoric, nitrous, and paratoluenesulfonic acids. On the contrary, removal of acetonoxime protection demands by refluxing with 20' (w/v) hydrochloric acid.

The invention is described in the following by nonlimiting examples.

EXAMPLE I 1. 3.1 g (14 mmoles of 1-ethoxyethylideneaminooxy-4-bromo-butene-2 (khomutov A. R. and Khomutov R. M. (1986) *Bioorgan. Khim.*, Russ., v. 12, No. 12, p. 1662–1674) was added to a solution of 2.26 g (2 mmoles) of β-cyclodextrin in a mixture of 18.7 ml water and 1.3 ml of 10 N NaOH and heated under nitrogen on a boiling water bath with intensive stirring until the pH turned neutral (usually 60–90 min). On cooling an oil separated. The product was washed with cold water and dissolved in 50 ml of i-PrOH and 4 ml of 5.0 N, HCl was added. After a 30-minute incubation at 20° C., the liquid was decanted and the residual oil crystallized with absolute i-PrOH. The precipitation was filtered and washed with absolute i-PrOH and dried over P$_2$O$_5$/KOH in vacuo, resulting in 2.80 g (90% yield) of (I). The amount of aminooxy groups was determined (Korpela, T. K. and Makela M. J. (1981) *Anal. Biochem.* v.110, No. 2, p. 251–258) and was 2.8 mmols/g, the low value indicating that only primary hydroxyl groups had reacted. NMR (Jeol-400, DMSO-d$_6$):

2. 7.7 g (35 mmoles) of 1-ethoxyethylideneaminooxy-4-bromobutene-2 was added to a solution of 5.6 g (5 mmoles) of β-cyclodextrin in a mixture of 70 ml of water and 3.4 ml of 10 N NaOH and mixed with a magnetic stirrer at 20° C. After two days, 10 ml of i-PrOH was added and stirring continued at 20° C. until the pH turned neutral (usually about 5–8 days). The solution was evaporated to dryness in vacuo, the residual oil washed with cold water and dissolved in 50 ml of i-PrOH and 10 ml of 5.0 N HCl was added. After a 30 minute incubation at 20° C., the liquid was decanted and the residual oil crystallized with absolute i-PrOH. The precipitation was filtered and washed with absolute i-PrOH and dried over P$_2$O$_5$/KOH in vacuo, resulting in 3.56 g (50% yield) of (I). The amount of aminooxy groups determined as above was 2.26 mmols/g NMR data identical to that in ex.I.1.

EXAMPLE II

2.8 g (12 mmoles) of 1-ethoxyethylideneaminooxy-4-bromo-butene-2 was added to a solution of 1.96 g (2 mmoles) of α-cyclodextrin (Sigma) in a mixture of 18.9 ml of water and 1.1 ml of 10 N-NaOH and heated under nitrogen on a boiling water bath with intensive stirring until pH turned neutral (usually 60–90 min). The oil which separated on cooling was washed with cold water and dissolved in 50 ml i-PrOH. To this solution 4 ml of 5.0 N HCl was added. After 30 min incubation at 37° C., the liquid was decanted and the residual oil crystallized with i-PrOH. The precipitation was filtered, washed with absolute i-PrOH and dried over P$_2$O$_5$/KOH in vacuo resulting in 2.21 g (69% yield) of II. The amount of aminooxy groups determined as above was 3.25 mmoles/g. NMR (Jeol-400, DMSO-d$_6$):

EXAMPLE III

3.54 g (16 mmoles) of 1-ethoxyethylideneaminooxy-4-bromobutene-2 was added to a solution of 2.6 g (2 mmoles) of γ-cyclodextrin (Fluka) in a mixture of 18.5 ml of water and 1.5 ml of 10 N NaOH and heated under nitrogen on a boiling water bath with intensive stirring until the pH turned neutral (usually 60–90 min). The oil which separated on cooling was washed with cold water and dissolved in 50 ml of i-PrOH and 4 ml of 5.0 N HCl was added. After a 30-minute incubation at 20° C., the liquid was decanted and the residual oil crystallized with i-PrOH. The precipitation was filtered and washed with abs. i-PrOH and dried over P$_2$O$_5$/KOH in vacuo, resulting in 3.76 g (95% yield) of III. The amount of aminooxy groups determined as above was 2,86 mmoles/g. NMR (Jeol-400, DMSO-d$_6$):

EXAMPLE IV

3.1 g (14 mmoles) of 1-ethoxyethylideneaminooxybutylbromide (Nedospasov A. A and Khomutov R. M. (1976) *Izv. AN SSSR Ser. Khim.* (in Russian) No. 9, p. 2113–2115) was added to a solution of 2.26 g (2 mmoles) of β-cyclodextrin in a mixture of 18.7 ml water, 0.21 g (1.4 mmoles) of NaI and 1.3 ml of 10 N. NaOH and heated under nitrogen on a boiling water bath with intensive stirring until the pH turned neutral (12–18 hrs). The oil separated on chilling was washed with cold water and dissolved in 50 ml of i-PrOH. To this solution 4 ml of 5.0 N HCl was added, after 30 min incubation at 20° C. the liquid was decanted and the residual oil crystallized upon abs. i-PrOH treatment. The precipitation was filtered and washed with abs. i-PrOH and dried over $P_2O_5$/KOH in vacuum, that gave 1.66 g (58% yield) of IV. The amount of aminooxy groups determined as above was 2.20 mmoles/g. NMR (Jeol-400, DMSO-$d_6$): 10.99 (m, $H_2N$—O—), 4.84 (m, $C_1$—H), 4.02 (m, $H_2NO$—$CH_2$—), 3.76–3.38 (mm, $C_3$—H, $C_6$—H, $C_5$—H, $C_2$—H, $C_4$—H), 1.62 (m, —$CH_2$—$CH_2$—). NMR (Jeol-400, $D_2O$): 4.92 (m, $C_1$—H), 3.95 (m, $H_2NO$—$CH_2$—), 3.71–3.45 (mm, $C_3$—H, $C_6$—H, $C_5$—H, $C_2$—H, $C_4$—H), 1.59 (m, —$CH_2$—$CH_2$—).

EXAMPLE V

To a solution of 1.5 g of (IV) in 15 ml of $H_2O$-aceton mixture (1:1, V/V), diluted acqueous ammonia was added to a pH of 5–6. Then the reaction mixture was incubated for 2 h at 20° C. After evaporation to dryness, the residue was treated with water, the semi-solid product was separated and crystallized twice from water. The precipitate was filtered off, dried in vacuo over $P_2O_5$/KOH and 1.1 g (7% yield) of (V) was obtained. NMR (Jeol-400, DMSO-$d_6$): 4.83 (m, $C_1$—H), 3.92 (m, =NO—$CH_2$—), 3.75–3.22 (m, $C_3$—H, $C_6$—H, $c_5$—H, $C_2$—H, $C_4$—H), 1.77 (m, $(CH_3)_2C$=), 1.59 (m, —$CH_2$—$C_2$—).

EXAMPLE VI

To a solution of 10.6 mg pyridoxal-5'-phosphate ("Merck") in 1.24 ml 0.1 N NaOD in $D_2O$, 20 mg of (IV) was added and the reaction mixture was incubated for 2 hr. at 20° C. The compound (VI) was obtained with a yield being close to quantative. NMR (Jeol-400, $D_2O$): 8.39 (m, H—C=N—O—), 7.70 (m, α-H), 4.85 (m, $C_1$—H), 4.74 (m, —$CH_2$—O—P—), 4.33 (m, $H_2NO$—$CH_2$—), 3.72–3.32 (m, $C_3$—H, $C_6$—H, $C_5$—H, $C_2$—H, $C_4$—H), 2.58 (m, α-$CH_3$), 1.58 (m, —$CH_2$—$CH_2$—).

EXAMPLE VII

To a solution of 0.74 g (4.5 mmoles) of 2-ethoxyethylideneamino-oxyethylmercaptane (Khomutov A. R. and Khomutov R. M. (1986) *Bioorg. Khim.* (Russ.) v. 12, No. 12, p. 1662–1674) in 2.0 ml abs. MeOH was added 2.22 ml of 2 M MeONa/MeOH, after evaporation in vacuum to dryness the residue was dissolved in a mixture of 9.5 ml abs. DMSO and 0.5 ml MeOH and added to a solution of 1.95 g (1.5 mmoles) of mono-6-O-tosyl-β-cyclodextrin (Matsui Y. and Okimoto A. (1978) *Bull. Chem. Soc.* (Japan) v. 51, No. 10, p. 3030–3034) in 15 ml abs. DMSO. The reaction was kept for 8 hr at 20° C., then 1.2 ml of 2 M AcOH in DMSO was added and the solution evaporated to dryness in vacuum. The residual oil solidified after water treatment, the precipitate was filtered off, washed with cold water, recrystallized twice from water and dried in vacuum over $P_2O_5$/KOH to give 1.3 g (yield 67%) of VII. NMR (Jeol-400, DMSO-$d_6$): 4.86 (m, $C_1$—H), 3.97 (q, $CH_3$—$CH_2$—O—), 3.94 (t, =NO—$CH_2$—), 3.79–3.33 (mm, $C_3$—H, $C_6$—H, $C_5$—H, $C_2$—H, $C_4$—H), 2.79 (m, —$CH_2$—$CH_2$—S—, 1.87 (s, $CH_3$—), 1.23 (t, $CH_3$—$CH_2$—O—).

EXAMPLE VIII

1.25 g (1.0 mmoles) of (VII) were suspended in 20 ml of 1 N HCl, heating to 50° C. gave clear solution, which was evaporated to dryness in vacuum. The residual oil solidified upon treatment with abs. i-PrOH The precipitate was filtered off, washed with abs. i-PrOH and dried over $P_2O_5$/KOH in vacuum that gave 0.80 g (65% yield) of (VIII). The amount of aminooxy groups determined as above was 0.88 mmoles/g. NMR (Jeol-400, DMSO-$d_6$): 4.85 (m, $C_1$—H) 4.12 (t, $H_2NO$—$CH_2$—), 3.82–3.33 (mm, $C_3$—H, $C_6$—$HC_5$—H—$C_2$—H, $C_4$—H), 2.86 (m, $CH_2$—$CH_2$—S)

EXAMPLE IX

To a solution of 0.62 g (0.5 mmoles) of (VIII) in 8.0 ml of a $H_2O$-acetone cocktail (1:1, V/V), a diluted water $NH_3$ solution was added to pH 5–6, and the reaction mixture was incubated for 2 h at 20° C. After evaporation to dryness, the residue was crystallized twice from water. The precipitate was filtered off, dried in vacuum over $P_2O_5$/KOH and 0.5 g (80% yield) of IX as obtained. NMR (Jeol-400, DMSO-$d_6$): 4.85 (m, $C_1$—H), 4.04 (t, =NO—$CH_2$—), 3.79–3.36 (mm, $C_3$—H, $C_6$—H, $C_5$—H, $C_2$—H, $C_4$—H), 2.77 (m, $CH_2$—$CH_2$—S), 1.80 (d, $CH_3$—).

EXAMPLE X

Mono-6-(4-ethoxyethylideneaminooxybutyl)thio-6-deoxy-β-cyclodextrin was obtained as is described for (VII) starting from 1.95 g (1.5 mmoles) of mono-6-O-tosyl-β-cyclodextrin and 0.85 g (4.5 mmoles) of 4-ethoxyethylideneaminooxyethylmercaptan (Nedospasov A. A. and Khomutov R. M. (1976) *Izv. AN SSSR Ser. Khim.* (in Russian) No. 9, p. 2113–2115) that gave 1.56 g (80% yield) of (X). NMR (Jeol-400, DMSO-$d_6$) 4.84 (m, $C_1$—H), 3.95 (q, $CH_3$—$CH_2$—O—), 3.80 (t, =NO—$CH_2$—), 3.75–3.31 (mm, $C_3$—H, $C_6$—H, $C_5$—H, $C_2$—H, $C_4$—H), 2.68 (m, $CH_2$—$CH_2$—S) 1.87 (d, $CH_3$—), 1.56 (m —$CH_2$—$CH_2$), 1.23 (t, $CH_3$—$CH_2$—O—).

EXAMPLE XI

Mono-6-(4-aminooxybutyl)thio-6-deoxy-β-cyclodextrin hydrochloride (XI)

Mono-6-(4-aminooxybutyl) thio-6-deoxy-β-cyclodextrin hydrochloride was obtained as is described for (VIII) starting from 1.3 g (1.0 mmoles) of (X) that gave 1.0 g (75% yield) of (XI). NMR (Jeol-400, DMSO-$d_6$): 10.85 (m, $H_2NO$—), 4.83 (m, $C_1$—H), 3.99 (m, $H_2NO$—$CH_2$—), 3.63–3.31 (mm, $C_3$—H, $C_6$—H, $C_5$—H, $C_2$—H, $C_4$—H), 1.59 (m, —$CH_2$—$CH_2$).

EXAMPLE XII

The acetonoxime of mono-6-(2-aminooxyethyl) thio-6-deoxy-y-β-cyclo-dextrin was obtained as is described for (IX) starting from 0.7 g of (XI) that gave 0.55 g (78% yield) of (XII). NMR (Jeol-400, DMSO-$d_6$): 4.82 (m, $C_1$—H), 3.89 (t, =NO—$CH_2$—), 3.61–3.32 (mm, $C_3$—H, $C_6$—H, $C_5$—H, $C_2$—H, $C_4$—H), 2.92 (m, $CH_2$ $CH_2$—S), 1.78 (d, $CH_3$—), 1.52 (m, —$CH_2$—$CH_2$—).

EXAMPLE XIII

Figure 1:
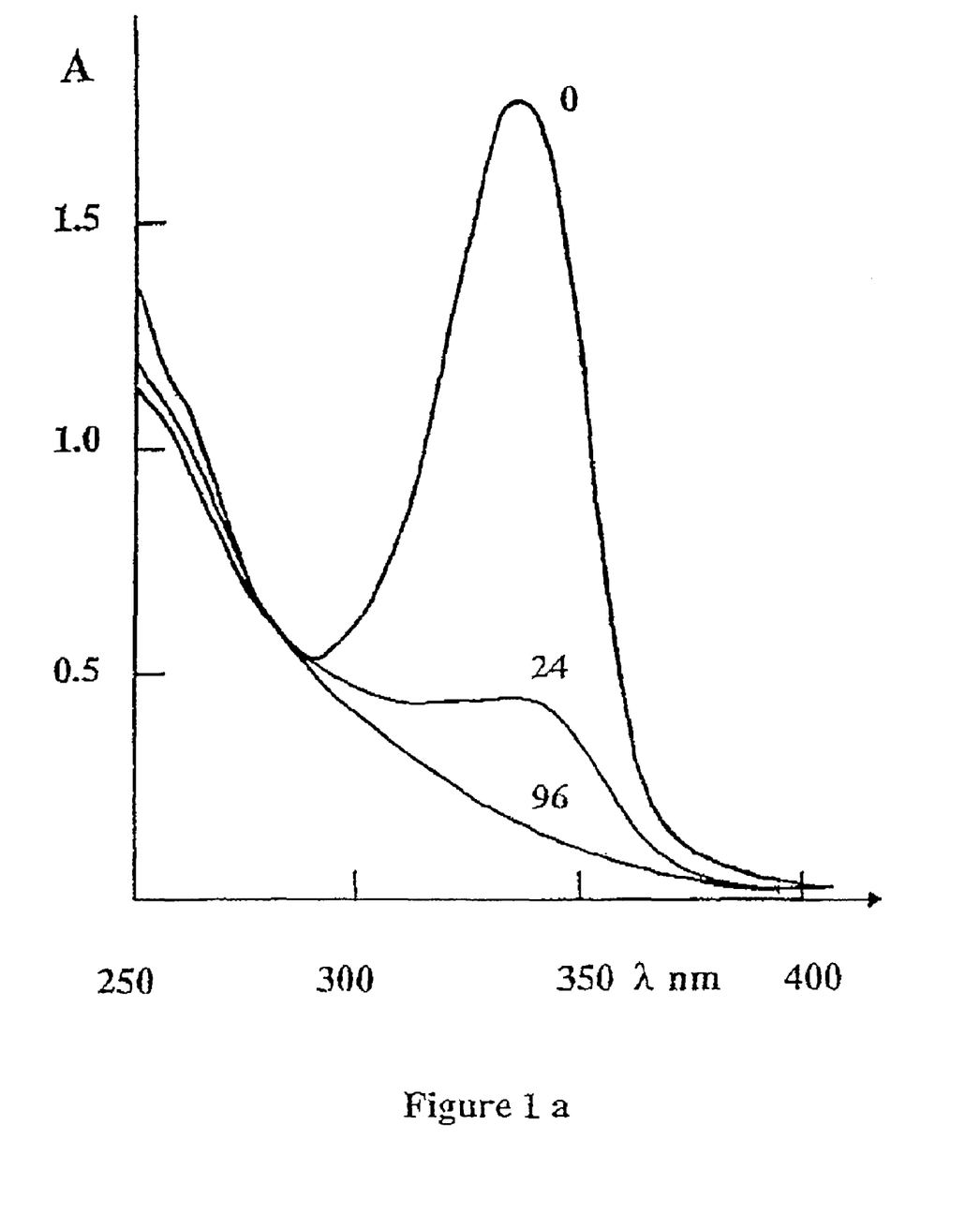
FIG. 1a. Time course of the UV spectra (optical path length 1 mm) of a reaction mixture containing 1 mM 4-thiouracil in 100 mM 4-aminooxy-2-butenyl-beta-cyclodextrin (I; see Example I.2) at pH 7.0. Incubation at 20° C. is indicated as hours.
FIG. 1b. Time course of the UV spectra (optical path length 1 mm) of a reaction mixture containing 1 mM 4-thiouracil and 100 mM 1-aminooxybutane at 20° C. at pH 7.00. Incubation time (hours) is indicated.

A 1 mM solution of 4-thiouracil (Lacheama, Brno, Czechoslovakia) was incubated at 20° C. within a 0.1 M solution of 4-aminooxy-2-butenyl-β-CD (I) at neutral pH. The UV-spectra were recorded at certain time intervals using cuvettes of 1 mm optical path length (FIG. 1a). This reaction was compared with the reaction of 4-thiouracil with 1-aminooxybutane under the same reaction conditions (FIG. 1b). The results show significantly higher velocity of reaction with the aminooxy-2-butenyl-β-CD.

EXAMPLE XIV

Figure 2A:
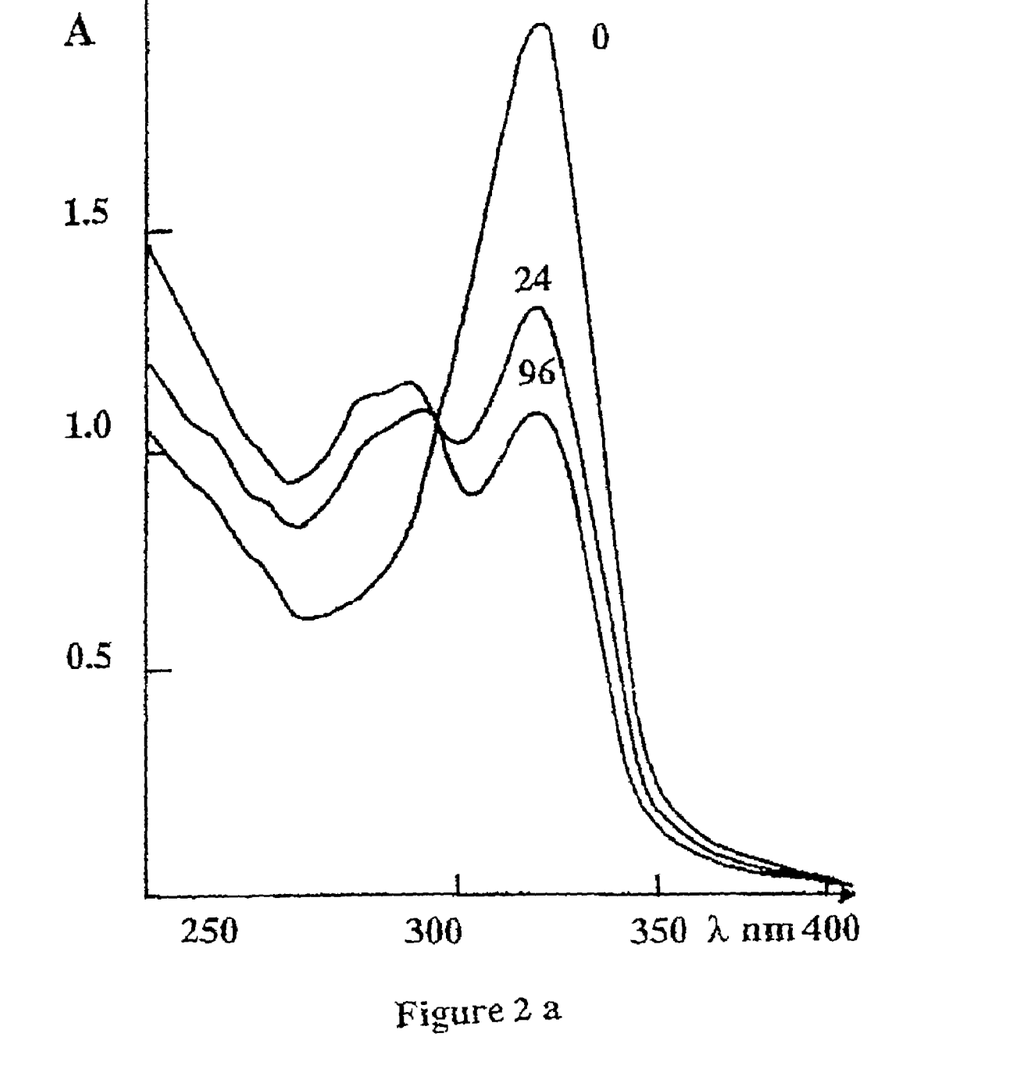
FIG. 2a. Time course of the UV spectra (optical path length 1 mm) of a reaction mixture containing 1 mM 6-mercaptopurineriboside with 100 mM 4-aminooxy-2-butenyl-beta-cyclodextrin (see Example I.2). Incubation time (hours) is indicated.
Figure 2B:
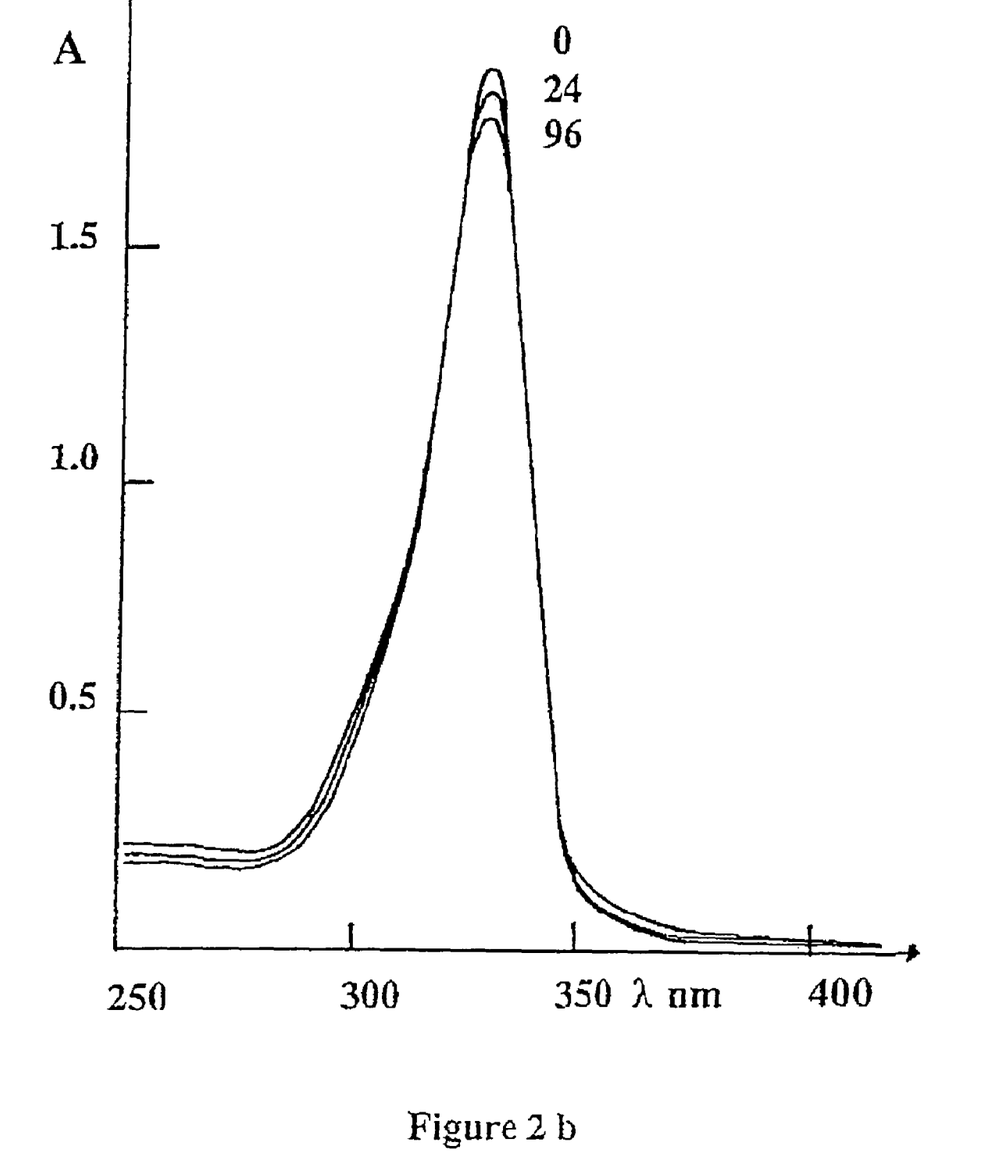
FIG. 2b. Time course of the UV spectra (optical path length b 1 mm) of a reaction mixture containing 1 mM 6-mercaptopurineriboside with 100 mM 1-aminooxybutane at pH 7.00. Incubation time (hours) is indicated.

A 1 mM solution of 6-mercaptopurine riboside (Sigma Chem. Co., USA) was incubated at 20° C. within 0.1 M of 4-aminooxy-2-butenyl-β-CD (I). At certain time intervals UV-spectra were recorded in cuvettes of 1 mm optical path (FIG. 2a) The similar reaction with 1-aminooxybutane (FIG. 2b) showed drastically higher reaction rates with the CD-derivative. its easy introduction into different sites of the CD molecules with different spacer arms make the aminooxy-CDs and their derivatives promising for the construction of catalytically active CDs.

The compounds of formula 1 can be prepared in different ways, and the present invention is also directed to the processes for the preparation of the novel compounds of the formula 1. Such processes are:

a) alkylation of a corresponding CD derivative with an aminooxy-protected, reactively substituted aminooxy derivative, for example with a compound of the formula 3':

wherein $R_2$, $R_3$ and $R_4$ are independently hydrogen, or a substituent (see Croft et. al. supra) having no reactive functional group, being typically alkyl, such as $C_1$–$C_6$— alkyl, or aryl, such as phenyl, benzyl or tolyl, whereby at least one of the positions 6, 3 and/or 2 contains a hydroxy group, preferably the 6-hydroxy group, W means $OC_2H_5$ or $CH_3$, m and Y are as defined above and Z is a reactive group, such as Cl, Br, I, tosyl or mesyl, and optionally removing the protecting group. In this case a compound of the formula 1 is obtained, wherein X is O. In the above formula, when W is $OC_2H_5$, the compound (3) is protected in the form of the 1-ethoxy-ethylideneaminooxy derivative, and when W is $CH_3$' in the form of the acetone oxime derivative.

What is claimed is:

1. Aminooxy-cyclodextrin compounds of the formula 1:

$$CD—(X—Y—ONH_2)_n \quad (1)$$

wherein
CD is a mono- or polydeoxy α-, β- or γ-cyclodextrin, carrying in its 6-, 3- and/or 2-position the aminooxy function containing group $(X—Y—ONH_2)$, and wherein Y is a linker group between the aminooxy group and the mono- or polydeoxy-CD-group,
X is a functional group or an atom necessary to connect the linker Y and the deoxy CD group, or Y is a direct bond when X is a direct bond, and
n is greater than or equal to 1, but less than or equal to 18, 21 or 24 for α-, β- or cyclodextrin, respectively.

2. The compound according to claim 1, wherein Y and X are both direct bonds.

3. The compound according to claim 1, wherein Y is a linear or branched alkylene, alkenylene with one or more double bonds which may be either isolated or conjugated, alkynylene with one or more triple bonds which may be either isolated or conjugated, or arylene or arylalkylene, whereby the alkylene, alkenylene and alkynylene may be linear or branched, and one or more of the chain members (methylene groups) may be replaced by —NH—, —O—, —S—, —S—S—, —C(O)NH, —C(O)O—, —OP(O)(OH) O—, —S(O)—, —SO₂—, or —CHR—, where R is alkyl, aryl, —OR', —NH₂, —NHR', —NR'₂, —OH, —COOH, or —ONH₂ groups and where R' is alkyl, aryl, or acyl.

4. The compound according to claim 1 or 3, wherein X is selected from the group consisting of —O—, —S—, —NH—, —NR"—, —OCO—, —NH—O—, =NO—, —NHC(O)—, —OP(O)(OH)O—, and —R"C=NO—, where R" is linear or branched lower alkyl.

5. The compound according to claim 3, wherein Y is alkylene containing 2–12 C-atoms, wherein one or more of the chain members may be replaced by —NH—, —O—, —S—, —C(O)NH—, —C(O)O—, or CHR$_1$ wherein R$_1$ is methyl, ethyl or propyl and X is —O—, —S—, —NH—, —OC(O)—, or —NH—C(O)—.

6. The compound according to claim 1, wherein one or more hydroxyl groups of the aminooxy cyclodextrin at 6-, 3-, and/or 2-position(s) are substituted with a group selected from the group consisting of H$_2$N—, HS—, —COOH, alkoxy-, aryloxy-, and acyloxy, and wherein said alkoxy-, aryloxy-, and acyloxy- can contain H$_2$N—, HS—, or —COOH.

7. The aminooxy-cyclodextrin compounds of claim 1, wherein the aminooxy group is in the form of ethoxy-ethylidene or methyl-ethylidene protected aminooxy.

8. The compounds according to claim 3, where the alkylene, alkenylene, and alkynylene contain 2 to 12 carbon atoms in the chain.

9. The compounds of claim 6, where the alkoxy is a $C_1$–$C_6$ alkoxy, the aryloxy is phenyloxy, benzyloxy or tolyloxy, and the acyloxy originates from $C_1$–$C_6$ carboxyl or benzoic acids.

* * * * *